(12) United States Patent
Kerschbaumer et al.

(10) Patent No.: US 7,006,126 B2
(45) Date of Patent: Feb. 28, 2006

(54) COLOR ANALYZING APPARATUS WITH POLARIZED LIGHT SOURCE

(75) Inventors: Harald Kerschbaumer, Klaus (AT); Walter Pokorny, Thüringen (AT); Gottfried Rohner, Altstätten (CH); Graham Pye, Genk (BE)

(73) Assignees: Ivoclar Vivadent AG, Schaan (LI); Shade Analyzing Technologies, Inc., Darien, CT (US)

( * ) Notice: Subject to any disclaimer, the term of this patent is extended or adjusted under 35 U.S.C. 154(b) by 664 days.

(21) Appl. No.: 10/157,936

(22) Filed: May 31, 2002

(65) Prior Publication Data

US 2002/0196438 A1  Dec. 26, 2002

Related U.S. Application Data

(60) Provisional application No. 60/307,001, filed on Jul. 20, 2001, provisional application No. 60/327,906, filed on Oct. 9, 2001.

(30) Foreign Application Priority Data

Jun. 1, 2001  (DE) ................................. 101 26 887

(51) Int. Cl.
*H04N 7/18* (2006.01)
(52) U.S. Cl. ............................. 348/66; 348/61; 348/68
(58) Field of Classification Search .................. 348/66, 348/61, 68; 356/326
See application file for complete search history.

(56) References Cited

U.S. PATENT DOCUMENTS

| | | | |
|---|---|---|---|
| 3,861,044 A | 1/1975 | Swinson, Jr. .................. 32/17 |
| 4,096,217 A | 6/1978 | Roll ............................ 264/20 |
| 4,184,175 A * | 1/1980 | Mullane, Jr. .................. 348/66 |
| 4,247,202 A | 1/1981 | Failes .......................... 356/310 |
| 4,414,635 A | 11/1983 | Gast et al. ................... 364/526 |
| 4,541,419 A | 9/1985 | Osawa ......................... 128/78 |
| 4,575,805 A | 3/1986 | Moermann et al. ......... 364/474 |
| 4,623,973 A | 11/1986 | Hoffrichter et al. ......... 364/526 |
| 4,654,794 A | 3/1987 | O'Brien ...................... 364/413 |
| 4,836,674 A | 6/1989 | Lequime et al. ............. 356/319 |
| 4,881,811 A | 11/1989 | O'Brien ...................... 356/323 |
| 5,038,258 A | 8/1991 | Koch et al. .................. 362/237 |
| 5,055,040 A | 10/1991 | Clar ............................. 433/26 |
| 5,115,307 A * | 5/1992 | Cooper et al. ................ 348/66 |
| 5,124,797 A | 6/1992 | Williams et al. ............. 358/225 |
| 5,177,694 A | 1/1993 | Graham et al. ............. 364/526 |
| 5,273,429 A | 12/1993 | Rekow et al. .............. 433/215 |
| 5,340,309 A | 8/1994 | Robertson .................... 433/69 |
| 5,373,364 A | 12/1994 | Krzyminski ................. 356/405 |

(Continued)

FOREIGN PATENT DOCUMENTS

DE     33 45 465     6/1985

(Continued)

*Primary Examiner*—Allen Wong
(74) *Attorney, Agent, or Firm*—Winston & Strawn LLP (57) ABSTRACT

A light analyzer with a first light source configured and disposed for irradiating with a first light an object disposed at an object location. A second light source is configured and disposed for irradiating the object with a second light that is preferably polarized along a first axis. A light receiving element is configured and disposed for receiving the first and second light reflected from the object and comprising a sensing device that is configured for sensing and producing an image corresponding to the reflected light. The light receiving element preferably comprises a polarizing filter configured for polarizing the reflected second light along a second axis at an angle to the first axis for reducing glare and reflection.

21 Claims, 7 Drawing Sheets

U.S. PATENT DOCUMENTS

| | | | | |
|---|---|---|---|---|
| 5,383,020 | A | 1/1995 | Vieillefosse | 356/326 |
| 5,431,562 | A | 7/1995 | Andreiko et al. | 433/24 |
| 5,498,157 | A | 3/1996 | Hall | 433/26 |
| 5,570,702 | A | 11/1996 | Forman | |
| 5,598,843 | A | 2/1997 | Caisey et al. | 128/653.1 |
| 5,690,486 | A | 11/1997 | Zigelbaum | 433/29 |
| 5,745,229 | A | 4/1998 | Jung et al. | 356/73 |
| 5,759,030 | A | 6/1998 | Jung et al. | 433/29 |
| 5,766,006 | A | 6/1998 | Murljacic | 433/26 |
| 5,851,113 | A | 12/1998 | Jung et al. | 433/29 |
| 5,851,115 | A | 12/1998 | Carlsson et al. | 433/215 |
| 5,871,351 | A | 2/1999 | Jung et al. | 433/29 |
| 5,880,826 | A | 3/1999 | Jung et al. | 356/73 |
| 5,883,708 | A | 3/1999 | Jung et al. | 356/73 |
| 5,910,841 | A | 6/1999 | Masao | 356/369 |
| 5,914,786 | A | 6/1999 | Koé | 356/446 |
| 5,926,262 | A | 7/1999 | Jung et al. | 356/73 |
| 5,938,446 | A | 8/1999 | Andersson et al. | 433/223 |
| 5,961,324 | A | 10/1999 | Lehmann | 433/26 |
| 5,966,205 | A | 10/1999 | Jung et al. | |
| 5,967,775 | A | 10/1999 | Shahid et al. | 433/29 |
| 5,990,468 | A | 11/1999 | Cornuejols | 250/208.1 |
| 6,007,332 | A | 12/1999 | O'Brien | 433/26 |
| 6,032,071 | A | 2/2000 | Binder | 600/476 |
| 6,038,016 | A | 3/2000 | Jung et al. | 356/71 |
| 6,038,024 | A * | 3/2000 | Berner | 356/326 |
| 6,040,902 | A | 3/2000 | Jung et al. | 356/73 |
| 6,111,650 | A | 8/2000 | Rawicz et al. | 356/402 |
| 6,118,521 | A | 9/2000 | Jung et al. | 356/73 |
| 6,124,936 | A | 9/2000 | Okamoto | 356/406 |
| 6,132,210 | A | 10/2000 | Lehmann | 433/26 |
| 6,157,454 | A | 12/2000 | Wagner et al. | 356/407 |
| 6,188,471 | B1 | 2/2001 | Jung et al. | 356/73 |
| 6,190,170 | B1 | 2/2001 | Morris et al. | 433/215 |
| 6,206,691 | B1 | 3/2001 | Lehmann et al. | 433/26 |
| 6,210,159 | B1 | 4/2001 | Lehmann et al. | 433/26 |
| 6,222,620 | B1 | 4/2001 | Jung et al. | 356/73 |
| 6,233,047 | B1 | 5/2001 | Jung et al. | 356/73 |
| 6,239,868 | B1 | 5/2001 | Jung et al. | 356/73 |
| 6,244,863 | B1 | 6/2001 | Rawicz et al. | 433/26 |
| 6,246,479 | B1 | 6/2001 | Jung et al. | 356/419 |
| 6,254,385 | B1 | 7/2001 | Jung et al. | 433/26 |
| 6,264,470 | B1 | 7/2001 | Jung et al. | 433/29 |
| 6,750,971 | B1 | 6/2004 | Overbeck et al. | 356/405 |

FOREIGN PATENT DOCUMENTS

| | | |
|---|---|---|
| DE | 37 06 473 CA | 10/1988 |
| DE | 40 34 007 A1 | 4/1992 |
| DE | 195 34 517 A1 | 3/1997 |
| EP | 0360657 | 9/1989 |
| JP | 06028368 | 10/1992 |
| WO | WO 86/03292 | 6/1986 |
| WO | WO 94/20011 | 9/1994 |
| WO | WO 94/28447 | 12/1994 |
| WO | WO 99/56658 | 11/1999 |
| WO | WO 00/69333 | 11/2000 |

* cited by examiner

Fig. 8

COLOR ANALYZING APPARATUS WITH POLARIZED LIGHT SOURCE

CROSS-REFERENCE TO RELATED APPLICATIONS

The present application claims the benefit of U.S. Provisional Application No. 60/307,001, filed on Jul. 20, 2001, and U.S. Provisional Application No. 60/327,906, filed on Oct. 9, 2001, the content of which applications is hereby expressly incorporated herein by reference thereto.

FIELD OF THE INVENTION

The present invention relates to a color analyzing and setting apparatus and, in particular, a color analyzing apparatus for analyzing the color of a tooth surface while eliminating the effects of glare and reflection and for analyzing the structure of the tooth.

BACKGROUND OF THE PRESENT INVENTION

Color setting apparatuses for sensing the color of a tooth surface are known, and an example of is described in DE-OS 195 34 517. This publication discloses a light source for emitting light along three paths to irradiate a tooth surface, and three corresponding sensors each for sensing the respective brightness of one of three base colors. It is taught that evaluation or analysis of the sensed results should lead to the least possible color deviation from the available tooth colors.

It is further conventionally known that reflected light or reflections distort or falsely influence the evaluation or analysis results. The arrangement of the light sources at various angles and emission of light therefrom at various spectra permits some compensation of the tendency toward reflection.

It has long been known that, due to the reduced or modest peak-to-valley thickness of the tooth surfaces, reflections distort the color analysis. In order to maintain the least possible degree of reflection, it is known to apply titanium oxide powder on the tooth surface as a contrast powder. However, depending upon the strength or thickness of the applied layer, a distortion of the color analysis is possible.

In order to avoid the disadvantages of contrast powder, the use of a fluorescing color has been suggested (compare DE-OS 40 37 007) whereby the fluorescing color absorbs the green color and emits gold or red. However, a decided disadvantage of such a fluorescing color lies in the fact that the color is distorted so that a compensation therefor must be undertaken in the event that the light shift is to be captured or sensed. Also, it is difficult to apply the fluorescing color exactly in a uniform strength or thickness, as a result of which this approach has not heretofore found widespread acceptance.

In connection with the evaluation of the tooth surface structure, it is desirable, in contrast to the evaluation of the tooth surface color, to capture or sense shadows which reveal or indicate the structure. In this context, as well, the application of a contrast powder or fluorescing color leads to distortion as the shadowing or the like is thereby reduced or eliminated.

It has further already been suggested to use a rotatable polarization filter which, in accordance with the wishes of the user, can be configured to permit the polarized light reflectance to be passed therethrough or to be reduced in an infinitely variable manner. This approach, indeed, permits the comparison of a tooth surface with and without reflection. However, the analysis of the sensed result is strongly dependent upon the angle at which the light source irradiates the tooth surface. Those areas of the tooth surface remote from the light source are frequently darkened or cast in shadow in an arrangement in which the light source is disposed to the side of the tooth surface and, consequently, such areas of the tooth surface cannot readily be recognized or sensed.

SUMMARY OF THE PRESENT INVENTION

The present invention offers a solution to the challenge of providing a color sensing apparatus for sensing the color of a tooth surface, providing improvements in color analysis as well as in analysis of the structure of a tooth surface.

A preferred embodiment of the invention is a light analyzer camera with a housing that is configured for handheld use with a single hand. The camera has first and second light sources configured and disposed for irradiating light on an object disposed at an object location. The first light source preferably produces a substantially unpolarized light. The second light source produces a second light that is polarized along a first axis, preferably by employing a polarization filter. A light receiving element is configured and disposed for receiving the first and second light reflected from the object and comprises a sensing device that is configured for sensing and producing an image corresponding to the reflected light. The light receiving element has a polarizing filter configured for polarizing the reflected second light along a second axis at an angle to the first axis for reducing glare and reflection. Preferably an image is produced from the light from each of the light sources, and a timer associated with the light sources and receiving element activates the first and second light source sequentially for producing one of the first and second images before the other.

The preferred camera includes a light channel configured for allowing light to pass therethrough and for blocking light from entering the channel radially from other sources. The first and second light sources are disposed adjacent the light receiving element in this embodiment, along a direction angled towards the light channel, and preferably inclined forward towards the object location. Additionally, the first and second paths are preferably oriented at different angles with respect to the object position In a preferred method of imaging an object according to the invention, the object is irradiated with a first light from a source such as a camera. The first light reflected from the object is received in the source or camera, and a first image is produced, corresponding to the received first light. The object is irradiated with a second light from the source or camera, the second light being polarized along a first axis. The second light reflected from the object is passed through a polarization filter for polarizing the second light along a second axis and received to produce a second image corresponding to the received second light. Where the image from the first light can show the structure of the tooth in detail due to glare and reflections produced in the image, the image formed with the second light is free or more free from undesired reflections, allowing the color to be analyzed more accurately. Preferably, one of the lights is irradiated and received before the other, and the irradiation of each light is preferably conducted within about two seconds from each other. The preferred method also includes blocking light from being received from other than the source or camera. The preferred object comprises a tooth, and the images are generated electronically. When the source is a camera, the images may be viewed in the camera or can be electronically transferred to another location for viewing.

By using two light sources, which irradiate the tooth surface at a different time and from different angular orientations, shadows are compensated for which would arise during the production of pictures of the tooth surface upon illumination thereof by a traditional light source arrangement. Filtering of the light through a single polarization filter, as in the preferred embodiment, has been found not to disturb or hinder the evaluation of the shadowing on the tooth, which provides information on the tooth structure, where the light that irradiates the tooth surface does not pass through a polarization filter. The preferred embodiment is also advantageous in that the irradiation of the tooth surface with a light source having a polarization filter can produce a reflection-free picture of the tooth surface, while through the irradiation of the tooth surface with another light source without polarization filter and which is oriented at a different angle relative to the tooth from the other light source provides a good sensing and capture of the tooth structure.

The light sources are preferably configured as white light sources. In addition, preferably a reference sample is irradiated with the same light sources to provide reflections captured by the same capture or sensing device of a light receiving element for electronic comparison to the images of the teeth. The reference sample is preferably disposed at a location close to and below or above the tooth or teeth being irradiated.

The present invention also provides for irradiating or illuminating the teeth from two different sides thereof, improving the illumination thereof for color and structure capturing. In this manner, in connection with the sequential actuation of the light sources, the structure of the tooth can be substantially clearly recognized or sensed, such that the tooth model that is subsequently produced based on the images gathered can be made including the sensed tooth structure.

In accordance with the present invention, through the common receipt or capture of pictures, which are produced by the different light sources, an effective or practical monitoring or quality control of the light sources and their color spectrums can be undertaken. In this manner, a white card can be inserted in substitution of the tooth surface and the measured or sensed color value of each light source can be used for the white color comparison. Moreover, an optical lens is preferably disposed in the light path between the tooth surface and the capture or sensing device of the receiving element, and it is possible with this lens to focus the picture of the tooth surface onto the capture or sensing device, in order to produce a precise image of the tooth surface.

Light sources are preferably provided on opposite sides of the tooth. It is possible to place a light source with a polarization filter at an angle of approximately 45° relative to the tooth surface to irradiate the tooth surface from this angle. A further light source without a polarization filter can be disposed at an angle of about 70° relative to the tooth surface so that shadows are more defined in the image produced by this light source.

BRIEF DESCRIPTION OF THE DRAWINGS

The object and advantages of the present invention will appear more clearly from the following specification in conjunction with the accompanying schematic drawings, in which.

DETAILED DESCRIPTION OF THE PREFERRED EMBODIMENTS

Figure 1:
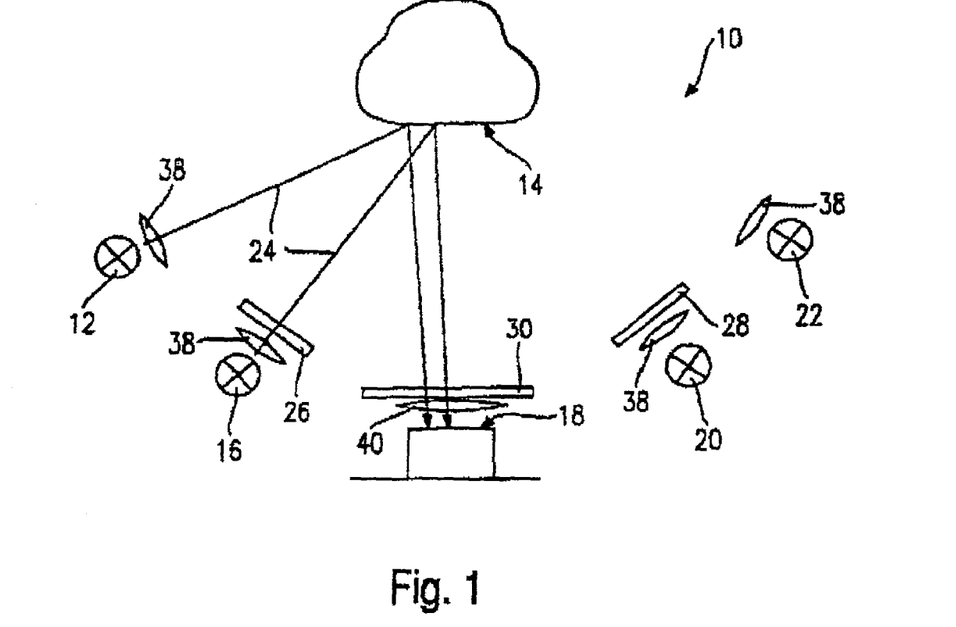
FIG. 1 is a schematic view of an embodiment of the color setting apparatus of the present invention.

The color setting apparatus 10, as shown in FIG. 1, includes a light source 12, which is disposed fairly substantially to the side of a tooth surface 14 for directing light from that side. Additionally, a light source 16 is provided, which is disposed toward the same side of the tooth surface as the light source 12 and is arranged at an angle relative to the tooth surface 14.

A capture or sensing device 18 is preferably disposed centrally and along a middle plane relative to the tooth surface 14, the sensing device 18 being operable to capture or sense the light reflected from the tooth surface 14.

A light source 20 is disposed symmetrically to the light source 16 and at an angle relative to the tooth surface 14 but is disposed on a different side of the tooth surface. In the embodiment of FIG. 1, the apparatus includes a fourth light source 22 disposed fairly substantially to the side of the tooth surface 14. The light source 22 is arranged to its respective side in a symmetric manner with regard to the location of the light source 12 on its respective side of the tooth surface. Preferably, light sources 16,20 are disposed at substantially the same angle from the sensing device 18. Similarly, light sources 12,22 are disposed at substantially the same angle from the sensing device 18, greater than the angle at which light sources 16,22 are disposed.

Each light source 12, 16, 20, and 22, preferably comprises a plurality of LEDs or light emitting diodes, so that a correspondingly high light output is available. All of the light sources 12, 16, 20, and 22, are preferably configured as white light emitting diodes. The light sources emit light 24 as shown, for example, schematically with respect to the light sources 12 and 16, and light 24 irradiates the tooth surface 14 and is reflected thereby to be captured or sensed by the sensing device 18.

In accordance with the embodiment shown, the light source 12 and the light source 22 are configured such that they directly irradiate the tooth surface 14 without a filter disposed therebetween. In contrast thereto, polarization filters 26,28 are disposed in front of light sources 16,20, respectively, between these light sources 16,20 and the tooth surface 14 along the path of light 24. Light 24 from these two light sources 16,20 passes through the polarization filters 26,28 before hitting the tooth surface 14. The polarization filters 26 and 28 are arranged, for example, to polarize the light in a vertical manner, although other directions of polarization are possible.

Moreover, in the light path between the tooth surface 14 and the sensing device 18, a further polarization filter 30 is disposed. The polarization orientation of the polarization filter 30 is, in contrast or perpendicular to the aforementioned polarization filters 26,28 for the light sources 16,20, i.e. horizontal in the embodiment shown. By this arrangement, reflections from the tooth surface can be suppressed in a conventional manner, if the light sources 16 and 20 are actuated.

Light sources 12, 16, 20, and 22 are preferably surrounded by reflectors for effecting an increase in the light output of the light sources, and light emitted from the light sources is collected by collecting lenses 38. Preferably, these collecting lenses 38 are so configured that they are color true and cause no distortion of the emitted color spectrums.

In a corresponding manner, a collecting lens 40 is disposed between the tooth surface 14 and the sensing device 18, which focuses the light for the formation of a picture of the tooth surface 14 onto the sensing device 18. The sensing device 18 comprises a CCD-sensor or any other desired suitable sensor.

Figure 2:
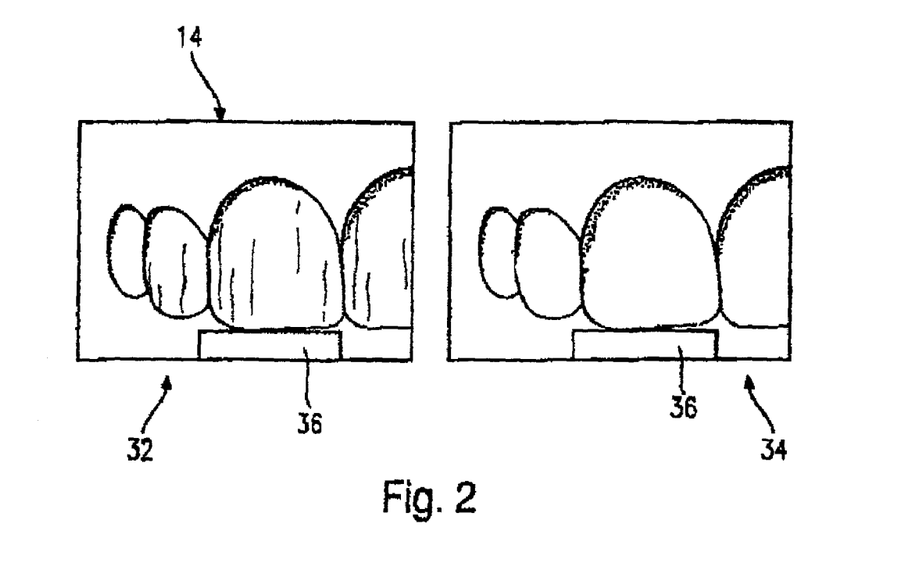
FIG. 2 is a schematic representation of the image generated by a capture or sensing device of a tooth surface, whereby the left-hand view shows the receipt of a tooth surface image via a light source not having a polarization filter and the right-hand view shows the receipt of a tooth surface image via a light source having a polarization filter.

FIG. 2 shows the manner in which a picture or image of the tooth surface 14 is captured or sensed. At least the substantially the whole of one tooth is preferably imaged, although at least two teeth can be viewed in the preferred embodiment. In the figures, between three and four teeth are included in each image. The left-hand view shown in FIG. 2 shows a picture 32, which is produced upon actuation of the light source 12. The reflections effected by the irradiation of the tooth surface by the light source 12 permit capture or recognition of the structure of the tooth surface. In contrast, the right-hand view shown in FIG. 2 shows a picture 34, which is produced upon actuation of the light source 16. By polarization of the light falling on the tooth surface in an orientation which is perpendicular to the polarization orientation of the reflections, the reflections are substantially reduced and substantially canceled and eliminated, making the determination of the specific color easier.

The pictures 32 and 34 show, in addition to the tooth surface 14, respective reference samples 36 which are inserted in immediate neighboring relation underneath the tooth surface. Preferably, the corresponding reference sample image results are arranged such that they are immediately adjacent those taken of the teeth.

Figure 3:
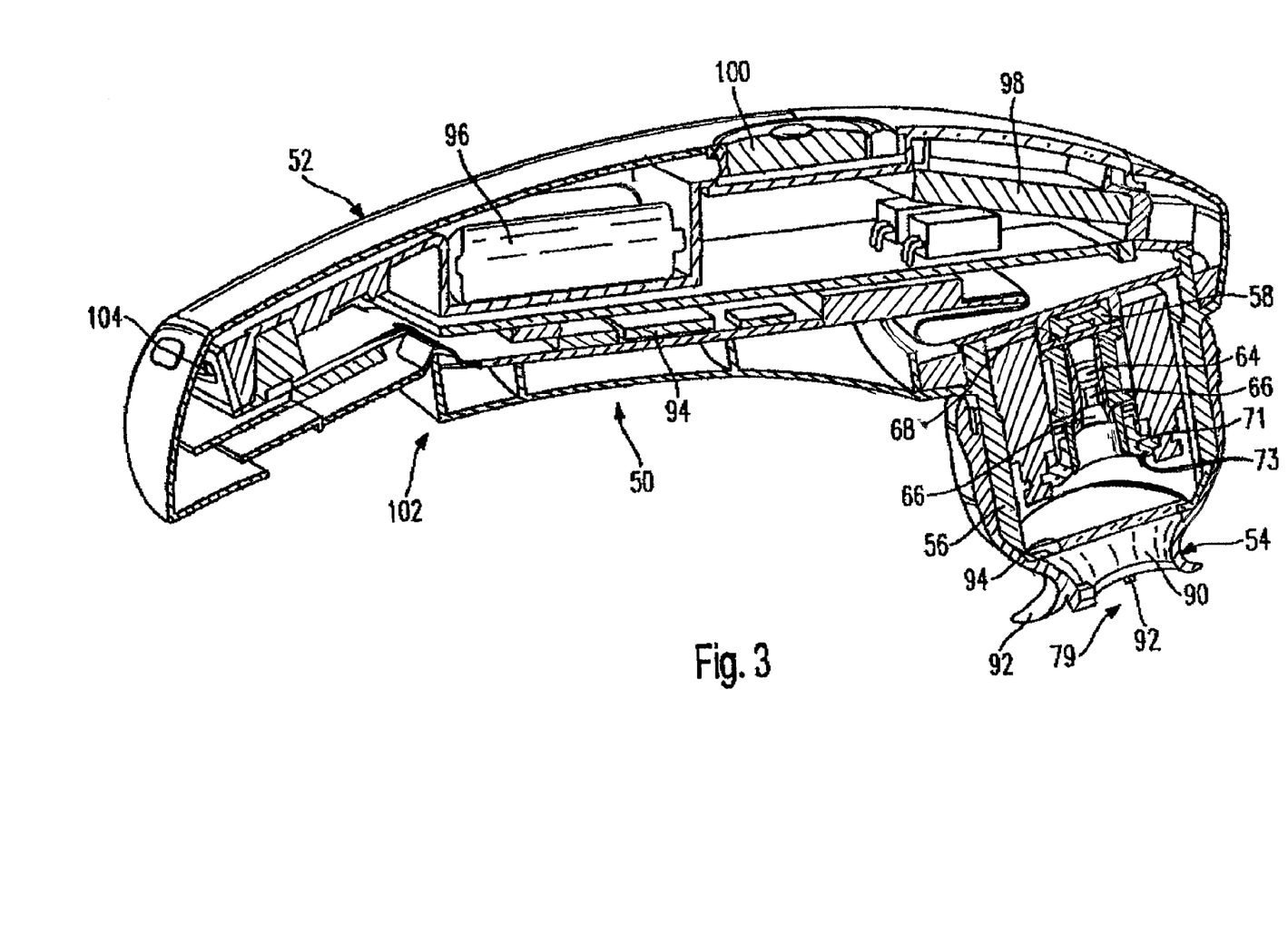
FIG. 3 is a side cutaway view of an embodiment of a dental camera constructed according to the invention.
Figure 4:
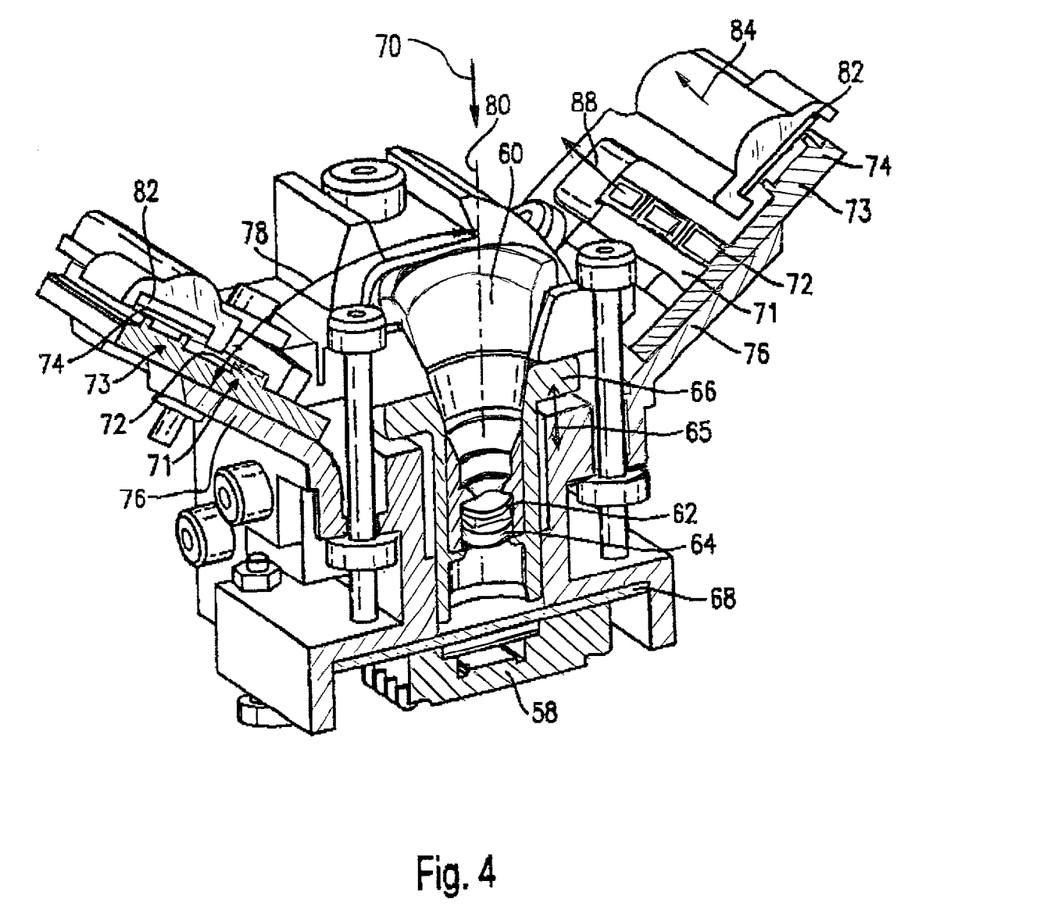
FIG. 4 is a cutaway view of the optical assembly thereof.

Referring to FIGS. 3 and 4, a preferred embodiment of a camera 50, including the color setting apparatus includes a housing 52 and a mouthpiece 54, which is fitted to a coupling member 56 of the housing 52. A sensing device 58, which preferably comprises a light receiving element such as a CCD chip, is preferably disposed substantially coaxially with a receiving light channel 60, which preferably blocks light from entering directly from the light sources within the camera.

Within the receiving light channel 60 are preferably disposed an infrared filter 62 and one or more camera lenses 64, which are mounted in a movably focus assembly 66. The focus assembly 64 is controlled preferably by electronics and a motor disposed within the camera 50 to move the focus assembly 64 in directions 65 to vary the distance between the lens 64 and the sensing device 58 in order to focus the received reflected light appropriately on the CCD to obtain a clear image. A receiving polarization-filter 68 is positioned along the reflected light path 70 ahead of the sensing device 58.

Light sources 72,74 are preferably disposed on each lateral side from the receiving light channel 60. The preferred light sources 71,73 comprise rows of LEDs configured for producing a white light. In the embodiment shown, the LEDs 72,74 are mounted on a supports 76 that extend along a direction angled towards the light channel, preferably in a forward direction towards an object position 79, at which the object to be pictured, such as teeth, is located for generating the images thereof. The supports 76 are preferably disposed at an angle 78 to the axis 80 of the light channel of about between 10° and 80°, more preferably about 40° and 50°. The preferred supports 76 are straight, although alternatives can be curved to obtain optimum placement of the light sources. The present embodiment includes a support on two sides of the receiving light channel 60, but a different number of supports and light source locations can be employed. For instance, one embodiment has light sources supported substantially surrounding all sides of the receiving light channel 60, and the supports can be connected as a single unit.

The location and configuration of the light sources 72,74 is preferably selected so that the light paths reach the object position 79 from different angles. This arrangement can provide to maximize the effectiveness of the light sources to illuminate the teeth for color analysis or for visualizing the tooth structure.

A source polarization-filter 82 is disposed along light paths 84 from LEDs 74. Source polarization filters 82 are preferably configured and oriented for polarizing the light from LEDs 74 along a first axis, whereas the receiving polarization-filter 68 is configured and oriented for polarizing the reflected light along a second axis that is different than the first axis. Preferably, these first and second axes of the source and receiving filters 82,68 are disposed at more than about 30° to each other, more preferably at more than about 45° to each other, more preferably at more than about 75° to each other, and most preferably at about a right angle to each other with respect to light paths 84,70 for best eliminating glare and disparate reflections from the image formed based on the light from sources 74. Lenses 86 are preferably cylindrical lenses an are disposed along light paths 84 for focusing and distributing the light from sources 74 to the teeth to properly illuminate the teeth.

Light sources 71 preferably produce substantially unpolarized light, with no polarization filter between the object position 79 and the LEDs 72 along light path 88. Alternatively, a polarization filter may be employed with light sources 71 with a relatively small or no difference in polarization axis orientation from the polarization axis of receiving polarization-filter 68. Additionally, in the embodiment shown in FIGS. 3 and 4, the second light source 72 does not include a lens in front of LEDs 72, but alternative embodiments also include lenses in the light path coming from these LEDs.

As shown in FIG. 3, the axis of the optical assembly of the camera 50 is oriented substantially coaxially with the mouthpiece 54 and coupling member 56, and main light channel 90 extends through the coupling member 56 and the mouthpiece 54 to permit the light from the light sources 72,74 to irradiate the teeth at the object position 79 and the light reflected by the teeth to return into the receiving light channel 60.

The mouthpiece 54 of the embodiment shown is configured to set the distance between the camera and the teeth and includes radially extending wings 92 configured for placement between the patient's lips and teeth or gums to block light from other sources from entering the camera and affecting the images produced. Bite protrusions 92 preferably extend forward from the wings for the patient to bite on, to help position the teeth with respect to the camera. The camera housing 52 preferably includes a protective transparent window, which is preferably disposed in the coupling portion 56 to prevent matter from the patient's mouth from entering the camera. A color reference sample 93 is disposed in the mouthpiece 54 to appear in the images generated of the teeth for comparison to the tooth color, as the sample 93 is of a known color, preferably white.

The preferred housing 52 also houses electronics 94 for controlling the camera functions, producing images from the signals from the CCD, and for storing and transferring data, including image files, to another computer or electronic device. The electronics comprise storage medium, such as a digital storage medium for storing the images and other data. Also contained within the housing are a power source 96, such as a battery or accumulator for powering the camera; a display 98, which is preferably a color LCD screen configured for displaying the image being presently generated and stored images; and a keypad 100 that provides an interface for a user to operate the camera. Preferably menu items related to camera control and information about the images are shown on the display 98. A protective transparent window is disposed outside of the display 98 for viewing the display preferably from a side of the camera 50 opposite from the object location. Many of these components are disposed within an elongated handle portion 102 of the housing, which extends preferably at a downward angle from the main light channel 90. Preferably at the bottom ends of the handle 102 is an interface 104, such as a USB interface, for connecting and transferring data to a computer or other electronic device.

The camera 50 preferably has a timer in the electronic circuitry that is configured for generating an image from the light from each of the first and second sources, preferably in response to a single push of a single key of the keypad 100 by the user. These images are preferably taken within about 2 seconds of each other, more preferably within about 1 second of each other, still more preferably within about ½ second or less.

As shown in FIGS. 3 and 4, the light sources are disposed adjacent a forward end of the receiving light assembly and receiving light channel 60, thus delivering the light directly to the object position, obviating the need for light conduits, such as fiber optics, prisms or mirrors to deliver the light to the object position 92. In an alternative embodiment, however, the one or more of the light sources is disposed well behind the front end of the receiving light channel, and the light from each light source is irradiated to the object position by conducting the light through optical conduits and by reflecting the light by with prisms and mirrors.

Figure 5:
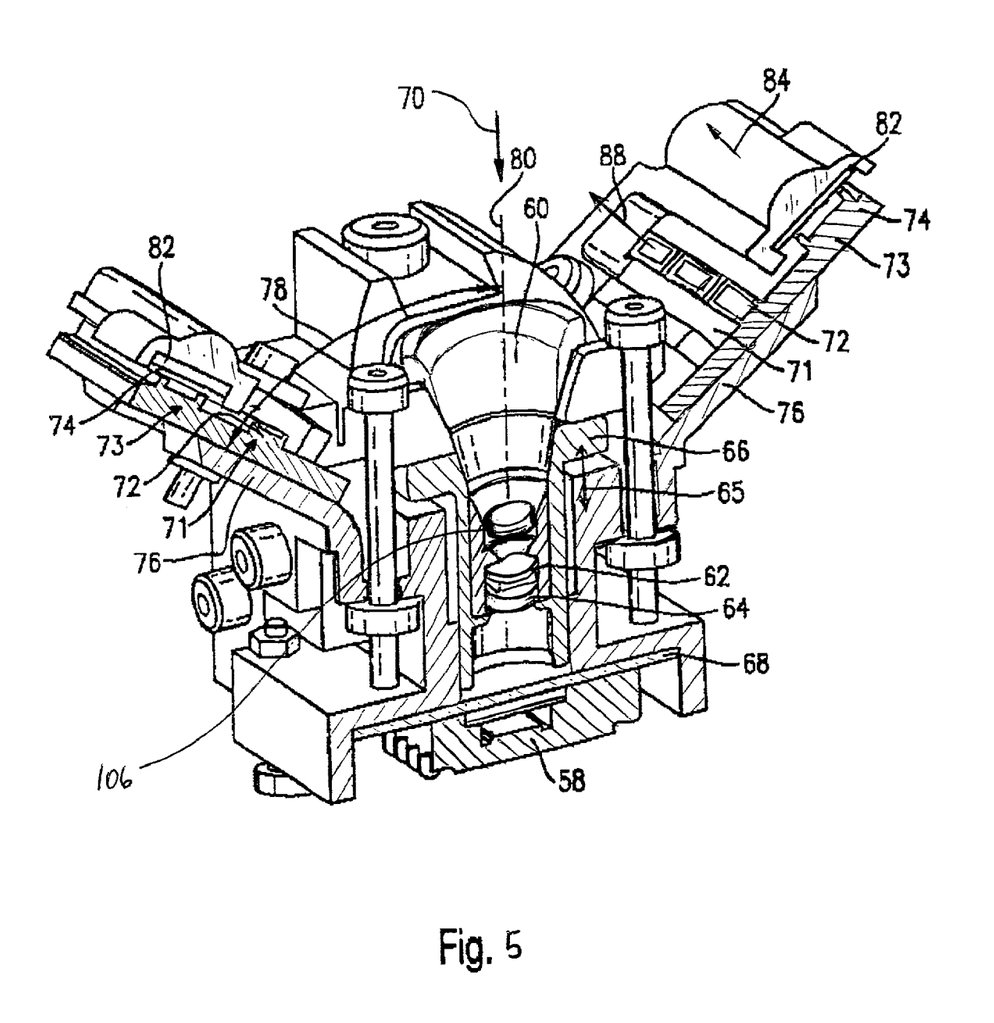
FIG. 5 is a cutaway view of the optical assembly of another embodiment with a zoom feature.
Figure 6:
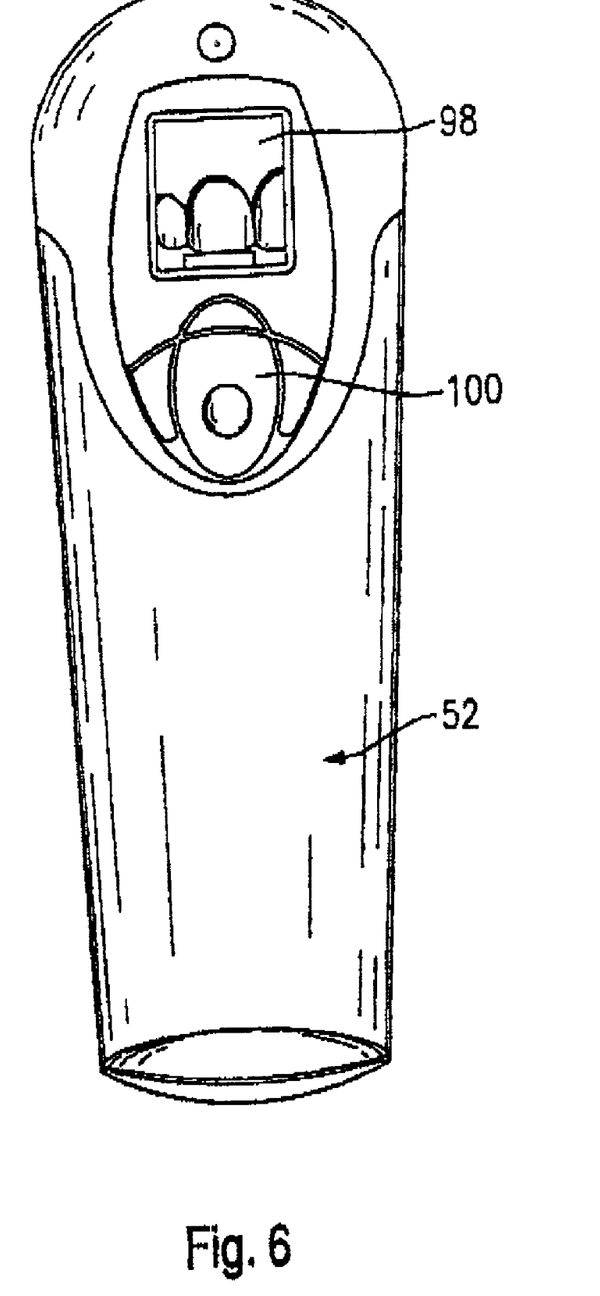
FIGS. 6–8 are back views of a camera according to the invention showing images produced by operating the zoom feature.
Figure 7:
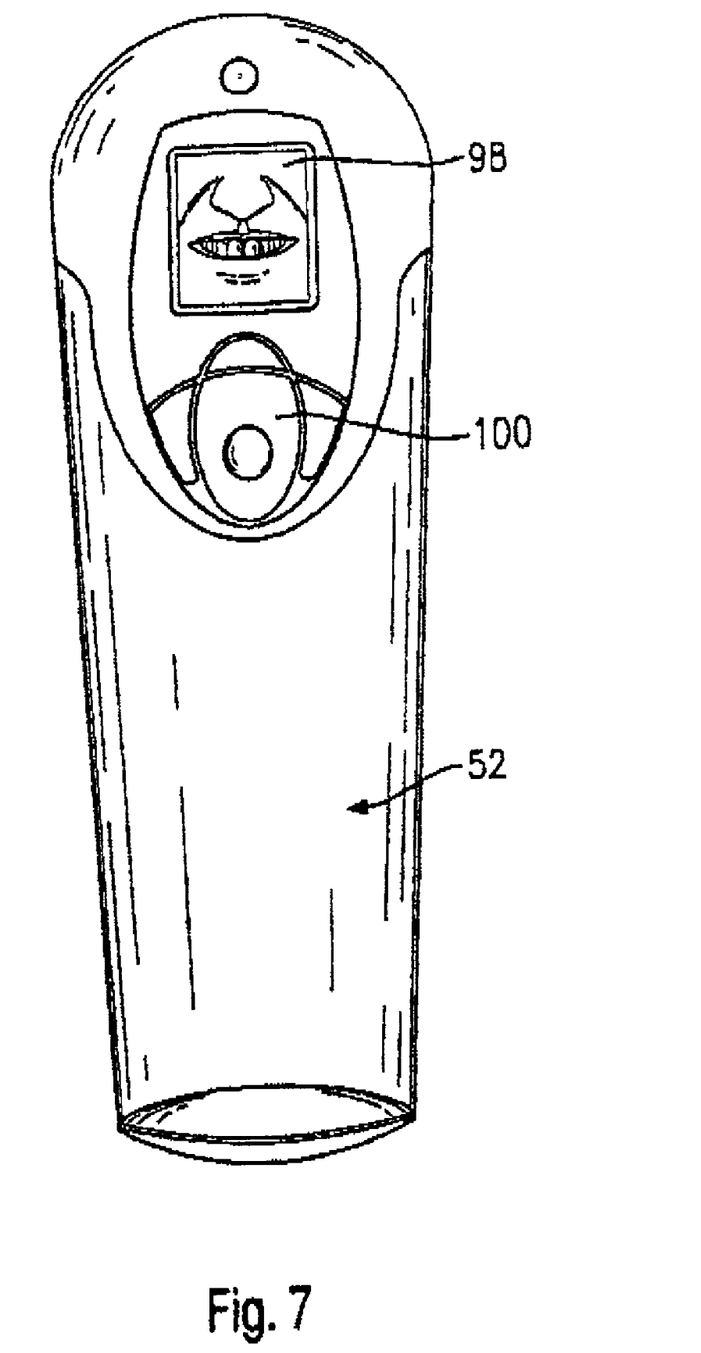
Figure 8:
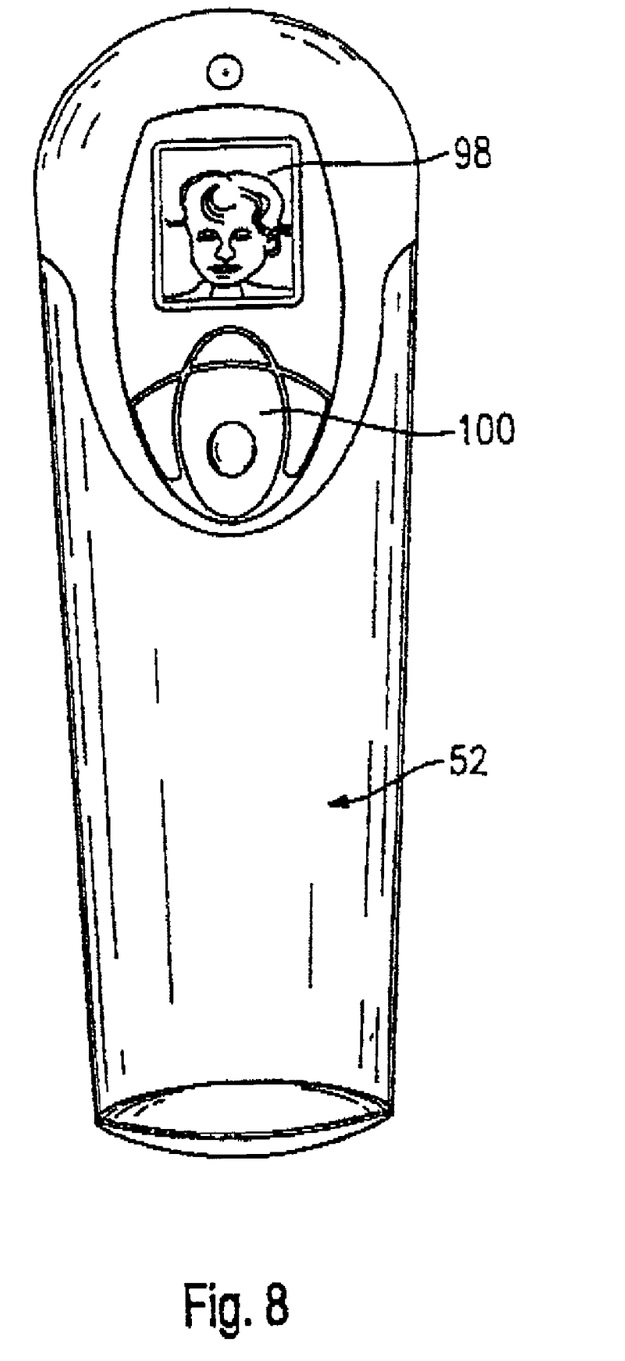

Referring to FIG. 5., the embodiment shown includes a zoom optical assembly 106 for varying the focal length of the camera. The zoom assembly 106 itself comprises one or more lenses and is controller preferably by the electronics 94 and a motor to vary the image from wide angle, as shown in FIG. 6, where one, two, three, or four teeth are shown in the image for example, to an image and lens arrangement that tends towards a telephoto, narrower-angle arrangement and image, for viewing the entire mouth, as shown in FIG. 7, or face of a patient, as shown in FIG. 8.

While illustrative embodiments of the invention are disclosed herein, it will be appreciated that numerous modifications and other embodiments may be devised by those skilled in the art. For example, whereas the preferred embodiment employs a polarization filter in one of the light sources, a light source of an alternative embodiment is configured or has a filter configured to block out or reduce light with a certain characteristic that is present in the light from the other light source. Therefore, it will be understood that the appended claims are intended to cover all such modifications and embodiments that come within the spirit and scope of the present invention.

What is claimed is:

1. A light analyzer, comprising:
   a first light source configured and disposed for irradiating with a first light an object disposed at an object location, thus generating first reflected light;
   a second light source configured and disposed for irradiating the object with a second light that is polarized along a first axis, thus generating second reflected light;
   a light receiving element configured and disposed for receiving both the first and second reflected light from the object and comprising a sensing device that is configured for sensing and producing a first image corresponding to the first reflected light, and a second image corresponding to the second reflected light, wherein the light receiving element comprises a polarizing filter configured for polarizing the second reflected light along a second axis at an angle to the first axis for reducing glare and undesired reflection; and
   a timer associated with the light sources and receiving element for activating the first and second light source sequentially for producing one of the first and second images before the other.

2. The light analyzer of claim 1, wherein the second light source comprises a polarization filter for polarizing the second light along the first axis.

3. The light analyzer of claim 1, wherein the first light source is configured such that the first light is substantially unpolarized along the first axis.

4. The light analyzer of claim 3, wherein the first light source is configured such that the first light is substantially unpolarized.

5. A dental camera, comprising:
   a camera housing;
   the light analyzer of claim 1 associated with the housing; and
   a light channel associated with the light analyzer and configured for allowing the first and second light to pass therethrough and for blocking light from entering the channel radially;
   wherein the first and second light sources are disposed adjacent the light receiving element along a direction that is angled towards the light channel.

6. The camera of claim 5, wherein the first and second light sources are disposed along a direction that is inclined forward towards the object location.

7. A light analyzer, comprising;
   first and second light sources configured and disposed for directing light along first and second light paths, respectively, towards an object disposed at an object position;
   a first filter configured for filtering light with predetermined qualities; and
   a light receiving element disposed along the light paths for receiving the light reflected from the object, the light receiving element comprising a sensing device that is configured for sensing characteristics of the light;
   wherein the light analyzer is configured such that the first filter is disposed along the first light path between the second light source and the object position, the second light path does not pass through the first light filter, and the light analyzer is configured for operating one of the light sources prior the other to generate separate images corresponding to the light from the first and second light paths, respectively.

8. The light analyzer of claim 7, wherein the first filter comprises a first polarization filter and the first and second light paths are disposed at different angles with respect to the object.

9. The light analyzer of claim 8, wherein:
the first polarization filter is configured for polarizing the light in a first polarization axis; and
the light analyzer comprises a second polarization filter disposed between object and the light receiving element along the second light path, the receiving polarization filter being configured for polarizing the light in a second polarization axis for reducing glare and reflection.

10. The light analyzer of claim 9, wherein the second polarization filter is also disposed along the first light path.

11. The light analyzer of claim 7, further comprising a camera housing that mounts the light sources, first filter, and light receiving element, wherein the housing is configured for handheld use.

12. A dental camera comprising:
a housing configured for handheld operation using a single hand; and
the light analyzer of claim 7.

13. A dental camera comprising:
a housing configured for handheld operation using a single hand;
first and second light sources mounted to the housing and, the light sources being separately operable and configured and disposed for directing light along first and second light paths towards an a tooth disposed at an object position, wherein the first and second paths are oriented at different angles with respect to the object position, and the second light source is configured for irradiating the light along the second path and polarized along a first axis;
a light receiving element mounted to the housing and disposed along the light paths for receiving the light reflected from the tooth and configured for forming first and second images corresponding to the received light from the first and second paths, respectively, the light receiving element comprising a polarization filter configured for polarizing the reflected light along a second axis at an angle to the first axis along the light path; and
a timer associated with the light sources and receiving element for activating the first and second light source sequentially for producing one of the first and second images before the other.

14. The light analyzer of claim 13, wherein the object is a tooth, and the light analyzer is a dental camera, which further comprises a color sensing device configured for sensing a color value of the tooth based on the images, and the light analyzer is such that the first image provides better information of tooth structure of the tooth than the second image, and the second image provides a more accurate color value of the tooth than the first image.

15. A method of imaging an object, comprising:
irradiating the object with a first light from a source;
receiving the first light reflected from the object in the source;
producing first image corresponding to the received first light;
irradiating the object with a second light from the source, wherein the second light is polarized along a first axis;
passing the second light reflected from the object through a polarization filter for polarizing the second light along a second axis;
receiving the second light from the polarization filter in the source; and
producing a second image corresponding to the received second light;
wherein one of the first light or second light is irradiated and received before the other is irradiated and received.

16. The method of claim 15, wherein the first and second lights are irradiated within about two seconds from each other.

17. The method of claim 15, further comprising blocking light from being received from other than the source.

18. The method of claim 15, wherein the object comprises a tooth.

19. The method of claim 15, wherein the source is located in a camera.

20. The method of claim 19, wherein the images are generated electronically and are viewable in the camera.

21. The method of claim 15, wherein the images are generated electronically and are transferred to another location for viewing.

* * * * *